United States Patent [19]

Kinoshita et al.

[11] Patent Number: 5,338,637
[45] Date of Patent: Aug. 16, 1994

[54] ELECTROPHOTOGRAPHIC PHOTORECEPTOR WITH PERYLENE AND STYRYL COMPOUNDS

[75] Inventors: Akira Kinoshita; Tomoko Suzuki; Kazumasa Watanabe, all of Hino, Japan

[73] Assignee: Konica Corporation, Tokyo, Japan

[21] Appl. No.: 898,133

[22] Filed: Jun. 15, 1992

[30] Foreign Application Priority Data

Jul. 3, 1991 [JP] Japan .................. 3-162958

[51] Int. Cl.$^5$ .......................... G03G 5/09
[52] U.S. Cl. .......................... 430/83; 430/59
[58] Field of Search .................. 430/59, 83

[56] References Cited

U.S. PATENT DOCUMENTS

| | | | |
|---|---|---|---|
| 4,556,622 | 12/1985 | Neumann et al. | 430/83 X |
| 4,606,988 | 8/1986 | Sasaki | 430/59 |
| 4,769,302 | 9/1988 | Ueda | 430/59 |
| 4,792,508 | 12/1988 | Kazmaier et al. | 430/59 |
| 5,183,718 | 2/1993 | Ueda | 430/59 |

FOREIGN PATENT DOCUMENTS 180956  7/1988  Japan ................. 430/59

*Primary Examiner*—Roland Martin
*Attorney, Agent, or Firm*—Jordan B. Bierman

[57] ABSTRACT

Disclosed is an electrophotographic photoreceptor which comprises a conductive substrate and a photoreceptive layer provided thereon, wherein the photoreceptive layer contains at least one of perylene compounds represented by Formula (I) and Formula (II) as the carrier-generating material, and a stryl compound represented by Formula (III) as the carrier-transport material,

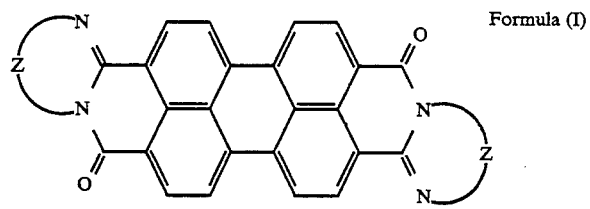

Formula (I)

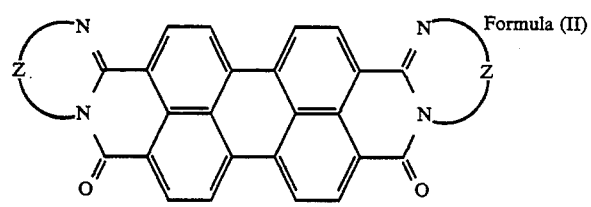

Formula (II)

wherein Z represents each a substituted or non-substituted divalent aromatic group,

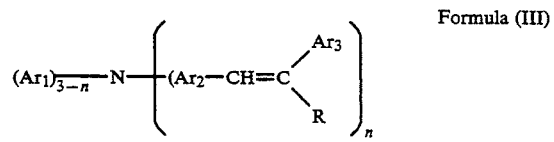

Formula (III)

wherein Ar1, Ar2 and Ar3 each represents a substituted or non-substituted aromatic group, n is an integer of 2 or 3.

An electrophotographic photoreceptor according to this invention is improved in photosensitivity, residual potential and photoreception speed.

6 Claims, 1 Drawing Sheet

ELECTROPHOTOGRAPHIC PHOTORECEPTOR WITH PERYLENE AND STYRYL COMPOUNDS

FIELD OF THE INVENTION

This invention relates to an electrophotographic photoreceptor, and more specifically to a highly sensitive photoreceptor particularly effective by used for printers, copiers and etc.

BACKGROUND OF THE INVENTION

As for electrophotographic photoreceptors, inorganic photoreceptors principally comprising an inorganic photoconductive material such as selenium, zinc oxide or cadmium sulfide have widely been used so far.

However, these inorganic photoreceptors have not always been satisfactory in their characteristics such as photosensitivity, thermal stability, moisture resistance and durability each required for copiers. For example, selenium is liable to deteriorate the characteristics for an electrophotographic photoreceptor, because selenium is crystallized by heat or a finger print stain. And, an electrophotographic photoreceptor applied with cadmium sulfide has been deteriorated in moisture resistance and durability. Further, an electrophotographic photoreceptor applied with zinc oxide has had a problem in durability. Still further, an electrophotographic photoreceptor applied with selenium or cadmium sulfide has also had a defect that they have been seriously limitative to their manufacture and manipulation from the viewpoint of toxity.

For improving the above-mentioned defects of the inorganic photoconductive materials, many studies have positively been made in recent years and the attempts were made to use various organic photoconductive materials in the photoreceptive layers of electrophotographic photoreceptors. For example, Japanese Patent Examined Publication (hereinafter referred to as JP Examined Publication) No. 50-10496/1975 describes an organic photoreceptor containing both polyvinyl carbazole and trinitrofluorenone. However, the photoreceptor described therein is not satisfactory for photoreceptivity and durability. Therefore, a function-separated type electrophotographic photoreceptor has been so developed as to assign the roles of a carrier-generating function and a carrier-transport function separately to the different materials, respectively.

In such an electrophotographic photoreceptor as mentioned above, the materials may be selected out of the wide ranges of them, so that any desired characteristics may be provided. It has, therefore, been expected to provide an organic photoreceptor high in photoreceptivity and excellent in durability.

As for the carrier-generating materials and the carrier-transport materials for the above-mentioned function-separated type electrophotographic photoreceptors, a variety of organic compounds have been proposed. Many carrier-generating materials have been put to practical application. They include, for example, a polycyclic quinone compound typified by dibromoanthanthrone, a pyrylium compound, an eutectic complex of a pyrylium compound and a polycarbonate, a squarium compound, a phthalocyanine compound and an azo compound. And, many carrier-transport materials have been put to practical application. They include, for example, a pyrazoline compound, a polyaryl alkane compound, a triphenylamine compound, a hydrazone compound, a diaminobiphenyl compound and a styrylbenzene compound.

Among the above-given compounds, JP Examined Publication No. 61-8423/1986 (U.S. Pat. No. 3,972,717) discloses a technique in which the perylene compounds represented by Formula [I] and/or [II] which are one of the elements constituting this invention are used as the carrier-generating materials of electrophotographic photoreceptors.

After this disclosure was made, the techniques of combining the carrier-generating materials with many kinds of carrier-transport materials have been reported. There are known techniques, for example, Japanese Pat. Publication Open to Public Inspection (hereinafter referred to as JP OPI Publication) No. 59-59686/1984 discloses a combination with a pyrazoline compound and a hydrazone compound, JP OPI Publication Nos. 61-275858/1986 (USP 4,587,189) and 63-180956/1988 disclose each a combination with a benzidine compound, JP OPI Publication No. 63-291061/1988 discloses a combination with a butadiene compound and USP-5,019,473 discloses a combination with a diphenyl methane compound.

As indicated above, some attempts have so far been tried. In the copiers, printers and facsimile equipments of the electrophotographic system, the demands for making faster in operations and smaller in sizes have recently been getting more serious. And, the photoreceptive materials have been more demanded to be improved in photosensitivity and, at the same time, to be made faster in photoreception response as a line speed is increased and a photoreceptive drum is made smaller in size. Therefore, the functional characteristics have not been satisfactory to meet the above-mentioned demands in any conventional techniques.

SUMMARY OF THE INVENTION

It is an object of the invention to provide an electrophotographic photoreceptor high in photosensitivity, low in residual potential and high in photoreception response speed so that a small-sized copier, a printer and a facsimile equipment can be provided.

Another object of the invention is to provide an excellent electrophotographic photoreceptor such as those capable of having a stable potential even in repetition use.

The present inventors have discovered the following facts. In making researches and developments of photoreceptors comprising a perylene compound as the carrier-generating material and when making combination use of the perylene carrier-generating material and a specific novel carrier-transport material, a highly photoreceptive and high-speed response characteristics can be obtained so as not to be expected from any conventional combination of a perylene compound with others and so as to be superior to any effects expected from the respective carrier-generating functions and carrier-transport functions each of any carrier-generating materials and carrier-transport materials, so that this invention has been achieved by the inventors.

BRIEF DESCRIPTION OF THE DRAWINGS

FIGS. 1(a–s) each of the cross-sectional views illustrating the typical examples of the layer arrangements of the photoreceptors of the invention.

In the drawings, the reference numerals indicate the following components;

1 = A conductive support

2 = A carrier-generating layer
3 = A carrier-transport layer
4' and 4" = Each of photoreceptive layers
5 = An interlayer

DETAILED DESCRIPTION OF THE INVENTION

The above-mentioned objects of the invention can be achieved by making combination use of a perylene compound represented by the following Formulas [I] and/or [II] as the carrier-generating materials and a styryl compound represented by the following Formula [III] as the carrier-transport material.

In Formulas [I] and [II], Z represents the group consisting of the atoms necessary to form a substituted or unsubstituted aromatic ring.

The desirable rings represented by Z include, for example, a benzene ring, a naphthalene ring, an anthracene ring, a phenanthrene ring, a pyridine ring, a pyrimidine ring, a pyrazole ring and an anthraquinone ring. Among them, the more desirable rings include, for example, a benzene ring and a naphthalene ring and, further desirably, a benzene ring. Z may have a substituent or may not have any substituent, however, those non-substituted are preferable.

The substituents for Z include, for example, an alkyl group, an alkoxy group, an aryl group, an aryloxy group, an acyl group, an acyloxy group, an amino group, a carbamoyl group, a halogen atom, a nitro group and a cyano group. Among them, an alkyl group is preferable.

In Formula [III], $Ar_1$, $Ar_2$ and $Ar_3$ represent each a substituted or non-substituted aromatic group; R represents a hydrogen atom or a substituted or a non-substituted aromatic group; and n is an integer of 2 or 3, especially, it is preferable when n is an integer of 2.

The desirable aromatic groups include, for example, a benzene group, a naphthalene group, an anthracene group, a thiophene group, a pyridine group and a carbazole group and, among them, the preferable groups are a benzene group and a naphthalene group. The substituents for the aromatic groups include, for example, an alkyl group, an aryl group, an alkoxy group, an aryloxy group, an acyl group, a halogen atom, an amino group and a cyano group and, preferably, an alkyl group having 1 to 6 carbon atoms, an alkoxy group having 1 to 6 carbon atoms, an acyl group having 1 to 6 carbon atoms, a halogen atom and an amino group.

It is also preferable when the substituents for $Ar_1$ are an ethyl group or plural methyl groups and the substituents for $Ar_3$ are a methyl group.

The compounds represented by Formula [I] or [II] can readily be synthesized in the following Reaction Formula (1).

The compounds represented by Formula [III] can readily be synthesized in the following Reaction Formula (2).

The typical examples of the compounds represented by Formula [I] or [II] will be given below.

Z is represented by Z denoted in the above-given formulas.

| No. | Z |
|---|---|
| A-1 | (benzene ring) |
| A-2 | (methylbenzene ring, CH₃) |

-continued

| No. | Z |
|---|---|
| A-3 |  |
| A-4 |  |
| A-5 |  |
| A-6 |  |
| A-7 |  |
| A-8 |  |
| A-9 |  |
| A-10 |  |
| A-11 |  |
| A-12 |  |
| A-13 |  |

-continued

| No. | Z |
|---|---|
| A-14 |  |
| A-15 |  |
| A-16 |  |
| A-17 |  |
| A-18 |  |
| A-19 |  |
| A-20 |  |
| A-21 |  |

The typical examples of the carrier-transport materials represented by Formula [III] will be given below.

| No | Ar$_1$ | Ar$_2$ | Ar$_3$ | R | n |
|---|---|---|---|---|---|
| B-1 |  |  |  | H | 2 |

-continued

| No | Ar₁ | Ar₂ | Ar₃ | R | n |
|---|---|---|---|---|---|
| B-2 | " | " | " |  | " |
| B-3 | " | " | " |  | " |
| B-4 | " | " |  |  | " |
| B-5 | " | " |  |  | " |
| B-6 | " | " |  | H | " |
| B-7 | " | " | " |  | " |
| B-8 | " | " | " |  | " |
| B-9 | " | " | " |  | " |
| B-10 | " | " |  |  | " |
| B-11 |  | |  | H | 2 |
| B-12 | " | " | " |  | " |
| B-13 | " | " | " |  | " |
| B-14 | " | " |  |  | " |

-continued

| No | Ar₁ | Ar₂ | Ar₃ | R | n |
|---|---|---|---|---|---|
| B-15 | " | " |  |  | " |
| B-16 | " | " |  | H | " |
| B-17 | " | " | " |  | " |
| B-18 | " | " | " |  | " |
| B-19 | " | " | " |  | " |
| B-20 | " | " |  |  | " |
| B-21 |  |  |  | H | 2 |
| B-22 | " | " | " |  | " |
| B-23 | " | " | " |  | " |
| B-24 | " | " |  |  | " |
| B-25 | " | " |  |  | " |
| B-26 | " | " |  | H | " |
| B-27 | " | " | " |  | " |

-continued

| No | Ar₁ | Ar₂ | Ar₃ | R | n |
|---|---|---|---|---|---|
| B-28 | " | " | " |  | " |
| B-29 | " | " | " |  | " |
| B-30 | " | " |  |  | " |
| B-31 |  |  |  | H | 2 |
| B-32 | " | " | " |  | " |
| B-33 | " | " | " |  | " |
| B-34 | " | " |  |  | " |
| B-35 | " | " |  |  | " |
| B-36 | " | " |  | H | " |
| B-37 | " | " | " |  | " |
| B-38 | " | " | " |  | " |
| B-39 | " | " | " |  | " |
| B-40 | " | " |  |  | " |

| No | Ar₁ | Ar₂ | Ar₃ | R | n |
|---|---|---|---|---|---|
| B-41 | 2,6-dimethylphenyl | -p-C₆H₄- | phenyl | H | 2 |
| B-42 | " | " | " | phenyl | " |
| B-43 | " | " | " | 4-methylphenyl | " |
| B-44 | " | " | 2-naphthyl | phenyl | " |
| B-45 | " | " | 4-methylphenyl | 4-methylphenyl | " |
| B-46 | " | " | 4-methoxyphenyl | H | " |
| B-47 | " | " | " | phenyl | " |
| B-48 | " | " | " | 4-methylphenyl | " |
| B-49 | " | " | " | 4-methoxyphenyl | " |
| B-50 | " | " | 2,5-dimethylphenyl | phenyl | " |
| B-51 | 2,5-dimethylphenyl | -p-C₆H₄- | phenyl | H | 2 |
| B-52 | " | " | " | phenyl | " |

-continued

| No | Ar₁ | Ar₂ | Ar₃ | R | n |
|---|---|---|---|---|---|
| B-53 | " | " | " |  | " |
| B-54 | " | " |  |  | " |
| B-55 | " | " |  |  | " |
| B-56 | " | " |  | H | " |
| B-57 | " | " | " |  | " |
| B-58 | " | " | " |  | " |
| B-59 | " | " | " |  | " |
| B-60 | " | " |  |  | " |
| B-61 |  |  |  | H | 2 |
| B-62 | " | " | " |  | " |
| B-63 | " | " | " |  | " |
| B-64 | " | " |  |  | " |

-continued

| No | Ar₁ | Ar₂ | Ar₃ | R | n |
|---|---|---|---|---|---|
| B-65 | " | " |  |  | " |
| B-66 | " | " |  | H | " |
| B-67 | " | " | " |  | " |
| B-68 | " | " | " |  | " |
| B-69 | " | " | " |  | " |
| B-70 | " | " |  |  | " |
| B-71 |  |  |  | H | 2 |
| B-72 | " | " | " |  | " |
| B-73 | " | " | " |  | " |
| B-74 | " | " |  |  | " |
| B-75 | " | " |  |  | " |
| B-76 | " | " |  | H | " |

-continued

| No | Ar₁ | Ar₂ | Ar₃ | R | n |
|---|---|---|---|---|---|
| B-77 | 3-F, 2-CH₃-phenyl | " | " | phenyl | " |
| B-78 | " | " | " | 4-CH₃-phenyl | " |
| B-79 | " | " | " | 4-OCH₃-phenyl | " |
| B-80 | " | " | 2,4-(CH₃)₂-phenyl | phenyl | " |
| B-81 | 4-CH₃-biphenyl | | 2,4-(CH₃)₂-phenyl | phenyl | 2 |
| B-82 | " | " | 4-Cl-phenyl | H | " |
| B-83 | " | " | " | phenyl | " |
| B-84 | " | " | " | 4-CH₃-phenyl | " |
| B-85 | " | " | 4-C₂H₅-phenyl | H | " |
| B-86 | " | " | 4-N(C₂H₅)₂-phenyl | H | " |
| B-87 | " | " | 4-COCH₃-phenyl | H | " |
| B-88 | " | " | naphthyl | H | " |

-continued

| No | Ar₁ | Ar₂ | Ar₃ | R | n |
|---|---|---|---|---|---|
| B-89 |  | " |  |  | " |
| B-90 | " | " |  | H | " |
| B-91 | — |  |  | H | 2 |
| B-92 | — | " | " |  | " |
| B-93 | — | " | " |  | " |
| B-94 | — | " |  |  | " |
| B-95 | — | " |  |  | " |
| B-96 | — | " |  | H | " |
| B-97 | — | " | " |  | " |
| B-98 | — | " | " |  | " |
| B-99 | — | " | " |  | " |
| B-100 |  | |  | H | " |
| B-101 | " | " | " |  | 2 |

-continued

| No | Ar₁ | Ar₂ | Ar₃ | R | n |
| --- | --- | --- | --- | --- | --- |
| B-102 | " | " | " | ―⟨phenyl⟩―CH₃ | " |
| B-103 | " | " | ―⟨naphthyl⟩ | ―⟨phenyl⟩ | " |
| B-104 | " | " | ―⟨phenyl⟩―CH₃ | ―⟨phenyl⟩―CH₃ | " |
| B-105 | " | " | ―⟨phenyl⟩―OCH₃ | H | " |
| B-106 | " | " | " | ―⟨phenyl⟩ | " |
| B-107 | " | " | " | ―⟨phenyl⟩―CH₃ | " |
| B-108 | " | " | " | ―⟨phenyl⟩―OCH₃ | " |
| B-109 | " | " | ―⟨2,5-dimethylphenyl⟩ | ―⟨phenyl⟩ | " |

In the invention, it is allowed to make combination use of the above-mentioned compounds and the other carrier-transport materials including, for example, a compound having both of a nitrogen-containing heterocyclic nucleus and the condensed cyclic nucleus typified by oxazole, oxadiazole, thiazole, thiadiazole and imidazole, a polyaryl alkane type compound, a pyrazoline type compound, a hydrazone type compound, a triarylamine type compound, a styryl type compound a styryltriphenyl amine type compound, a β-phenylstyryl triphenyl amine type compound, a butadiene type compound, a hexatoluene type compound, a carbazole type compound and a condensed polycyclic type compound.

Various types of photoreceptor constitution have been known.

Figure 1A:
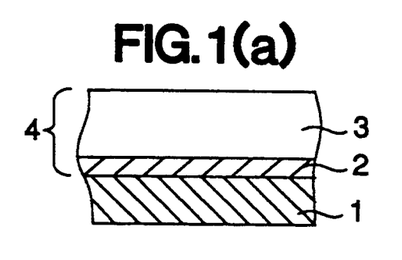
Figure 1B:
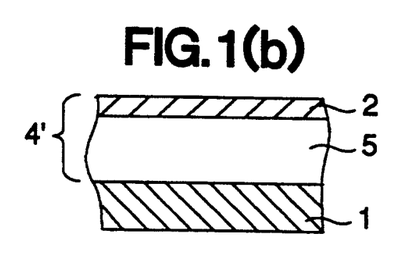
Figure 1C:
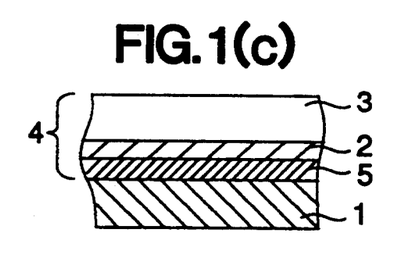
Figure 1D:
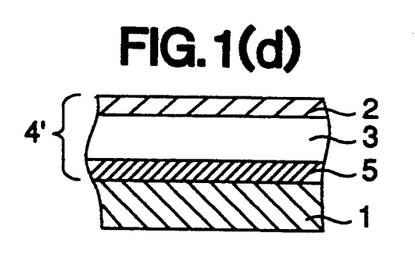
Figure 1E:
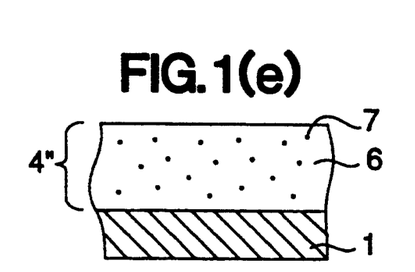
Figure 1F:
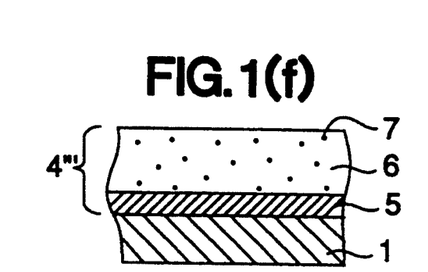

The photoreceptors of the invention can be of any one of the types. It is, however, desirable to be a laminated layer type or dispersion type of function-separated photoreceptor. In this case, the constitution thereof is usually those shown (in FIGS. 1(a) through 1(f). The layer arrangement shown in FIG. 1 (a) is that phoreceptive layer 4 was formed on conductive support by laminating carrier generating layer 2 on the conductive support and further laminating carrier-transport layer 3 thereon in turn. The layer arrangement shown in FIG. 1(b) is that photoreceptive layer 4' was so formed as to inversely arrange the carrier-generating layer 2 and carrier-transport layer 3. The layer arrangement shown in FIG. 1 (c) was that interlayer 5 was interposed between the photoreceptive layer 4 and conductive support 1 shown in the layer arrangement of FIG. 1 (b). The layer arrangement show in FIG. 1 (d) was that inter layer 5 was interposed between the photoreceptive layer 4' and conductive support 2 shown in the layer arrangement of FIG. 1 (b). The layer arrangement shown in FIG. 1 (e) is that photoreceptive layer 4" containing carrier-generating material 6 and carrier-transport material 7 was formed. And, the layer arrangement shown in FIG. 1 (f) is that interlayer 5 was interposed between the photoreceptive layer 4" and conductive support 1. In the constitution shown in FIGS. 1 (a) through 1 (f), the outermost layer is also allowed to have a protective layer.

In the formation of the photoreceptive layer, it is effective to use a method of coating a solution prepared by dissolving a carrier-generating material or a carrier-transport material independently or together with a binder and/or an additive.

However, the solubility of the carrier-generating materials are generally low. Therefore, in this case, it is effective to use a method of coating a solution prepared by dispersing finely grained carrier-generating material into a suitable dispersant by making use of a dispersing means such as a supersonic disperser, a ball-mill, a sand-mill or a homogenizer, or another method of forming a carrier-generating layer in a vacuum evaporation.

As for the solvents or dispersants applicable to form a photoreceptive layer, a wide range of those may be used.

They include, for example, butyl amine, ethylene diamine, N,N-dimethyl formamide, acetone, methyl ethyl ketone, cyclohexanone, tetrahydrofran, dioxane, ethyl acetate, butyl acetate, methyl cellosolve, ethyl cellosolve, ethylene glycol methyl ether, toluene, xylene, acetophenone, chloroform, dichlor methane, dichlor ethane, trichlor ethane, methanol, ethanol, propanol and butanol.

When making use a binder for forming a carrier-transport layer, any desired binders may be used for. Among them, the desirable binders include, particularly, a hydrophobic macromolecular polymer having a film-forming function. These polymers include, for example, the following ones, whereto the invention shall not be limited.

Polycarbonate
Polycarbonate Z resin
Acrylic resin
Methacrylic resin
Polyvinyl chloride
Polyvinylidene chloride
Polystyrene
A styrene-butadiene copolymer
Polyvinyl acetate
Polyvinyl formal
Polyvinyl butyral
Polyvinyl acetal
Polyvinyl carbazole
Styrene-alkyd resin
Silicone resin
Silicone-alkyd resin
Silicone-butyral resin
Polyesters
Phenol resin
Polyurethane
Epoxy resin
A vinylidene chloride-acrylonitrile copolymer
A vinyl chloride-vinyl acetate copolymer and
A vinyl chloride-vinyl acetate-maleic anhydride copolymer The ratio of the carrier-transport material to a binder is desirably within the range of 10 to 500 wt%. The carrier-generating layer thickness is within the range of 0.01 to 20μm and, preferably, 0.05 to 5μpm. The carrier-transport layer thickness is within the range of 1 to 100m and, preferably, 5 to 30μm.

To the photoreceptive layers relating to the invention, an antioxidant may be added for the purpose of preventing any ozone deterioration. Such antioxidants as mentioned above include, for example, hindered phenol hindered amine, paraphenylene diamine, aryl alkane, hydroquinone, spirochroman, spiroindanone and the derivatives thereof, an organic sulfur compound and an organic phosphorus compound.

The typical compounds thereof are given in, for example, JP OPI Publication Nos. 63-14154/1988, 63-18355/1988, 63-44662/1988, 63-50848/1988, 63-50849/1988, 63-58455/1988, 63-71856/1988, 63-71857/1988 and 63-146046/1988.

The above-mentioned photoreceptive layers are allowed to contain an electron-receptive material for the purposes of improving a photosensitivity, lowering a residual potential or reducing a fatigue in repetition use. The electron-receptive materials include, for example, succinic anhydride, maleic anhydride, dibromosuccinic anhydride, phthalic anhydride, tetrachlorphthalic anhydride, tetrabromophthalic anhydride, 3-nitrophthalic anhydride, 4-nitrophthalic anhydride, pyromellitic anhydride, mellitic anhydride, tetracyanoethylene, tetracyanoquinodimethane, o-dinitrobenzene, m-dinitrobenzene, 1,3,5-trinitrobenzene, p-nitrobenzonitrile, picric chloride, quinonechlorimide, chloranyl, bromanyl, dichlorodicyano-p-benzoquinone, anthraquinone, dinitroanthraquinone, 9-fluorenylidene malonodinitrile, picric acid, o-nitrobenzoic acid, p-nitrobenzoic acid, 3,5-dinitrobenzoic acid, pentafluorobenzoic acid, 5-nitrosalicylic acid, 3,5-dinitrosalicylic acid, phthalic acid, mellitic acid and other compounds each having a great electron affinity. The electron receptive materials are desirably added in a proportion within the range of 0.01 to 200 parts and, preferably, 0.1 to 100 parts to 100 parts by weight of a carrier-generating material used.

The conductive supports applicable to the invention include, for example, a metal plate or a metal drum and, besides, those made of a conductive polymer or a conductive compound such as indium oxide and a support comprising a base material such as paper sheet or a plastic film provided thereonto a thin metal layer of aluminum or palladium by a coating, evaporating or laminating means.

The photoreceptors of the invention have the above-mentioned constitution. Therefore, they are excellent in electric charging property, photosensitive characteristics and repetion use, as is obvious from the following examples.

EXAMPLES

Synthetic example

A mixture of 39.2 g of perylene-3,4,9,10-teracarboxylic dianhydride, 32.4 g of o-phenylenediamine and 800 ml of α-chloronaphthalene was reacted at 260° C. for 6 hours. After cooling the reacted matter, the resulting deposited crystals were filtrated. The resulting filtrate was washed repeatedly with methanol and then dried up with heating, so that 51.1 g of dark-green crystals could be obtained, (at a yield of 95.3%).

The resulting crystals were further so sublimated as to be refined, so that the mixture of the compounds represented by the following two formulas could be obtained.

-continued

The resulting photoreceptor is named Comparative Samples (1) and (2), respectively.

COMPARATIVE EXAMPLE (3)

The photoreceptor for comparison was prepared in the same manner as in Example 1, except that the carrier-generating material used in Example 1 was replaced by the following compound Z-3. The resulting photoreceptor is named Comparative Samples (3).

(Z-1)

(Z-2)

(Z-3)

EXAMPLE 1

A dispersion of 1 part of the carrier-generating material resulted in the above-described synthetic example and 50 parts of methyl ethyl ketone as a dispersant was made with a sandmill. The resulting dispersed solution was coated on an aluminum-evaporated polyester base with a wire-bar, so that a carrier-generating layer having a layer thickness of 0.3μm could be formed. Next, a solution was prepared by dissolving 1 part of carrier-transport material B-62, 1.4 parts of polycarbonate resin 'Panlite K1300' (manufactured by Teijin Chemical Co.) and a small amount of silicone oil 'KF-54' (manufactured by Shinetsu Chemical Co.) in 10 parts of 1,2-dichloroethane. The resulting solution was coated with a blade-coater and then dried up, so that a carrier-transport layer having a layer thickness of 22μm could be formed. The resulting photoreceptor is named Sample 1.

EXAMPLES 2 ~ 4

The photoreceptors of the invention were each prepared in the same manner as in Example 1, except that the carrier-transport material B-62 used in Example 1 was replaced by B-13, B-65 and B-53. The resulting photoreceptors are named Samples 2, 3 and 4, respectively.

COMPARATIVE EXAMPLES (1) ~ (2)

The photoreceptors for comparison were each prepared in the same manner as in Example 1, except that the carrier-transport material B-61 used in Example 1 was replaced by the following compounds Z-1 and Z-2.

Evaluation 1

The resulting samples were each evaluated by making use of a paper analyzer EPA-8100 (manufactured by Kawaguchi Electric Co.) in the following manner. First, a corona-discharge was applied under the conditions of $-6KV$ for 5 seconds and surface potential Va obtained immediately after applying an electric charge and surface potential Vi obtained after allowing the samples to stand for 5 seconds. Successively, an exposure was made to light so as to have a surface illumination intensity of 2 (lux) so as to obtain an exposure quantity $E_{\frac{1}{2}}$ which is required to have a surface potential of $\frac{1}{2}$ Vi and an exposure quantity $E_{600/100}$ which is required to lower the surface potential from $-600V$ to $-100V$, respectively. Further, a dark decay ratio D was also obtained from the formula of $D=100$ $(Va-Vi)/Va$ (%). The results thereof will be shown in Table-1.

Evaluation 2

The resulting samples were each loaded on a copier U-bix 1600 modified model (manufactured by Konica Corp.) and the potential $V_H$ in the unexposed area and potential $V_L$ in the exposed area were each obtained. Further, the $V_H$ and $V_L$ were also obtained after completing the repetition uses of 10000 times. The results thereof will be shown in Table-2.

TABLE 1

| Sample No. | Va (V) | Vi (V) | D (%) | $E_{\frac{1}{2}}$ (lux · sec) | $E_{600/100}$ (lux · sec) |
| --- | --- | --- | --- | --- | --- |
| Sample 1 | −1250 | −1030 | 17.6 | 1.3 | 2.4 |
| Sample 2 | −1210 | −980 | 19.0 | 1.5 | 2.8 |
| Sample 3 | −1260 | −1040 | 17.5 | 1.3 | 2.4 |
| Sample 4 | −1290 | −1090 | 15.5 | 1.1 | 2.2 |

TABLE 1-continued

| Sample No. | Va (V) | Vi (V) | D (%) | $E_{\frac{1}{2}}$ (lux · sec) | $E_{600/100}$ (lux · sec) |
| --- | --- | --- | --- | --- | --- |
| Comparative sample (1) | −1120 | −870 | 22.3 | 2.3 | 4.6 |
| Comparative sample (2) | −1130 | −860 | 23.9 | 3.0 | 5.8 |
| Comparative sample (3) | −1090 | −850 | 22.0 | 6.7 | 15.7 |

TABLE 2

| Sample No. | <Initial stage> | | <After 10000th repetition> | |
| --- | --- | --- | --- | --- |
| | $V_H$ (V) | $V_L$ (V) | $V_H$ (V) | $V_L$ (V) |
| Sample 1 | −620 | −60 | −620 | −60 |
| Sample 2 | −600 | −80 | −590 | −90 |
| Sample 3 | −620 | −60 | −620 | −65 |
| Sample 4 | −620 | −40 | −620 | −40 |
| Comparative sample (1) | −590 | −100 | −570 | −150 |
| Comparative sample (2) | −590 | −130 | −580 | −240 |
| Comparative sample (3) | −580 | −300 | −540 | −390 |

EXAMPLE 5

A solution was prepared by dissolving 1 part of carrier-transport material B-53 and 1.5 parts of polyester resin 'Biron 200' (manufactured by Toyobo Corp.) in 10 parts of 1,2-dichlorethane. The resulting solution was coated on an aluminum drum in a dip-coating method and then dried up, so that a carrier-transport layer having a layer thickness of 13μm could be formed.

On the other hand, 1 part of carrier-generating material A-2, 3.5 parts of polyester 'Biron 200' (manufactured by Toyobo Corp.) as the binder resin, 15 parts of monochlorobenzene as the dispersant and 35 parts of 1,2-dichlorethane were dispersed together by making use of a ball-mill and carrier-transport material B-53 was so added thereto so as to have a proportion of 75 wt% of the amount of the binder resin used. The resulting dispersed solution was coated on the carrier-transport layer in a spray-coating method, so that a carrier-generating layer having a layer thickness of 4μm could be formed.

The resulting photoreceptors were each evaluated in the same manner as in Evaluation 1, except that the charging polarity was changed into a positive polarity.

$Va = 1230$ (V)

$Vi = 1140$ (V)

$D = 15.4$ (%)

$E_{\frac{1}{2}} = 1.8$ (lux·sec)

$E_{600/100} = 3.3$ (lux·sec)

EXAMPLE 6

The carrier-generating material prepared in the foregoing synthetic example was vacuum-evaporated on an aluminum-evaporated polyester base, so that a carrier-generating layer having a layer thickness of 0.2μm could be formed.

Next, a solution was prepared by dissolving 1 part of carrier-transport material B-53, 1.2 parts of polycarbonate resin 'Eupiron Z200' (manufactured by Mitsubishi Gas-Chemical Co.) and a small amount of silicone oil 'KF-54' (manufactured by Shinetsu Chemical Co.) in 10 parts of 1,2-dichlorethane. The resulting solution was coated by making use of a blade-coater and then dried up, so that a carrier-transport layer having a layer thickness of 30μm could be formed.

The resulting photoreceptor is named Sample 6.

EXAMPLE 7

A photoreceptor of the invention was prepared in the same manner as in Example 6, except that carrier-generating material A-1 used in Example 6 was replaced by A-2.

The resulting photoreceptor is named Sample 7.

EXAMPLES 8 ~ 9

The photoreceptors of the invention were each prepared in the same manner as in Example 6, except that carrier-transport material B-53 used in Example 6 was replaced by B-43 and B-102 and the resulting photoreceptors are named Samples 8 and 9, respectively.

COMPARATIVE EXAMPLES (4) ~ (5)

The comparative photoreceptors were each prepared in the same manner as in Example 6, except that the carrier-generating materials used in Example 6 was replaced by the following compounds (Z-4) and (Z-5) and the resulting photoreceptors are named Comparative samples (4) and (5), respectively.

COMPARATIVE EXAMPLES (6) ~ (10)

The comparative photoreceptors were each prepared in the same manner as in Example 6, except that the carrier-transport material used in Example 6 was replaced by the following compounds (Z-6), (Z-7), (Z-8) and (Z-9) and (Z-10) the resulting photoreceptors are named Comparative Samples (6), (7), (8) (9) and (10), respectively.

(Z-4)

-continued

(Z-5)

(Z-6)

(Z-7)

(Z-8)

(Z-9)

(Z-10)

The resulting samples were each evaluated in the same manner as in Evaluation 1. The results thereof will be shown in Table-3.

TABLE 3

| Sample No. | Va (V) | Vi (V) | D (%) | $E_{\frac{1}{2}}$ (lux · sec) | $E_{600/100}$ (lux · sec) |
|---|---|---|---|---|---|
| Sample 6 | −1230 | −1100 | 10.6 | 0.8 | 1.5 |
| Sample 7 | −1180 | −970 | 17.8 | 1.1 | 2.0 |

TABLE 3-continued

| Sample No. | Va (V) | Vi (V) | D (%) | E½ (lux·sec) | E600/100 (lux·sec) |
|---|---|---|---|---|---|
| Sample 8 | −1240 | −1090 | 12.1 | 0.9 | 1.8 |
| Sample 9 | −1250 | −1100 | 12.0 | 0.9 | 1.8 |
| Comparative sample (4) | −1190 | −930 | 21.8 | 7.6 | 19.3 |
| Comparative sample (5) | −1220 | −910 | 25.4 | 22.5 | ∞ |
| Comparative sample (6) | −1230 | −1050 | 14.6 | 1.6 | 3.0 |
| Comparative sample (7) | −1210 | −1030 | 14.9 | 1.9 | 3.8 |
| Comparative sample (8) | −1030 | −740 | 28.2 | 2.1 | 4.2 |
| Comparative sample (9) | −1200 | −1010 | 15.8 | 2.6 | 4.5 |
| Comparative sample (10) | −1230 | −1050 | 14.6 | 1.7 | 3.3 |

As are obvious from the above-given examples, it was proved that the electrophotographic photoreceptors of the invention have each an extremely high photoreceptivity and an excellent potential stability even in repetition use.

Attached sheet (5)
Evaluation 3

For testing the high-speed respondence, A subject sample was loaded on a copier U-bix modified model 5076 (manufactured by Konica Corp.) and was then exposed to light under the negatively charged conditions. After completing the exposure, the surface potentials V0.2(V) and V0.5(V) were each measured at 0.2 (sec) and 0.5 (sec), respectively. The results thereof are shown in Table-4.

TABLE 4

| Sample No. | $V_{0.2}$ (V) | $V_{0.5}$ (V) |
|---|---|---|
| Sample 1 | −70 | −60 |
| Sample 2 | −90 | −80 |
| Sample 3 | −70 | −60 |
| Sample 4 | −60 | −50 |
| Sample 6 | −40 | −30 |
| Sample 7 | −70 | −50 |
| Sample 8 | −50 | −40 |
| Sample 9 | −50 | −40 |
| Comparative sample (1) | −130 | −100 |
| Comparative sample (2) | −150 | −130 |
| Comparative sample (3) | −450 | −350 |
| Comparative sample (4) | −220 | −150 |
| Comparative sample (5) | −425 | −270 |
| Comparative sample (6) | −110 | −70 |
| Comparative sample (7) | −150 | −90 |
| Comparative sample (8) | −170 | −100 |
| Comparative sample (9) | −160 | −120 |
| Comparative sample (10) | −100 | −70 |

As are obvious from the above-given examples, the photoreceptors of the invention can display the excellent characteristics in high-speed respondence.

What is claimed is:

1. An electrophotographic photoreceptor which comprises a conductive substrate and a photoreceptive layer provided thereon, wherein the photoreceptive layer contains at least one of perylene compounds represented by Formula (I) and Formula (II) as the carrier-generating material, and a stryl compound represented by Formula (III) as the carrier-transport material, Formula (I)

Formula (II)

wherein Z represents each a substituted or non-substituted divalent aromatic group, Formula (III)

wherein Ar1, Ar2 and Ar3 each represents a substituted or non-substituted aromatic group, n is an integer of 2 or 3.

2. The electrophotographic photoreceptor of claim 1, wherein Z of the Formula (I) and the Formula (II) is a substituted or non-substituted divalent group selected from the group consisting of a phenylene group, a naphthalenediyl group, an anthracenediyl group, a phenanthrenediyl group, a pyridinediyl group, a pyrimidinediyl group, a pyrazolediyl group and an anthraquinonediyl group.

3. The electrophotographic photoreceptor of claim 1, wherein Ar1, Ar2 and Ar3 of the Formula (III) is each a substituted or non-substituted divalent aromatic group selected from the group consisting of a phenylene group, a naphthalenediyl group, a thiophenediyl group, a pyridinediyl group and a carbazolediyl group and n is an integer of 2 to 3.

4. The electrophotographic photoreceptor of claim 1, wherein the perylene compound is a compound selected from the group consisting of Formula (IV) and Formula (V) as the carrier-generating material, Formula (IV)

Formula (V)

wherein $R_1$ is represented by an alkyl group having 1 to 6 carbon atoms, m is an integer of 0 or 2.

5. The electrophotographic photoreceptor of claim 2, wherein said stryl compound is represented by Formula (VI) as the carrier-transport material, wherein $Ar_1$, $Ar_2$ and $Ar_3$ each represents a substituted or non-substituted aromatic group.

6. An electrophotographic photoreceptor which comprises a conductive substrate and a photoreceptive layer provided thereon, wherein the photoreceptive layer contains at least one of perylene compounds is a compound selected from the group consisting of Formula (IV) and Formula (V) as the carrier-generating material, and a stryl compound represented by Formula (VI) as the carrier-transport material, Formula (IV)

Formula (V)

wherein $R_1$ is represented by an alkyl group having 1 to 6 carbon atoms, m is an integer of 0 to 2.

wherein $Ar_1$, $Ar_2$ and $Ar_3$ each represents a substituted or non-substituted aromatic group.

* * * * *